United States Patent [19]

Vogen

[11] Patent Number: 4,813,407

[45] Date of Patent: Mar. 21, 1989

[54] SESAMOID BONE CLAMP

[76] Inventor: Kenneth W. Vogen, 3780 Woodruff, Suite F, Long Beach, Calif. 90808

[21] Appl. No.: 892,125

[22] Filed: Jul. 30, 1986

[51] Int. Cl.[4] ............................................. A61F 5/04
[52] U.S. Cl. ............................... 128/92 VZ; 128/346
[58] Field of Search ................... 128/92 V, 321, 346, 128/92 R, 92 VZ, 92 VK, 322

[56] References Cited

U.S. PATENT DOCUMENTS

| | | | |
|---|---|---|---|
| 1,217,637 | 2/1917 | Rink | 128/92 VZ |
| 1,302,176 | 4/1919 | Klett | 128/92 VZ |
| 1,601,035 | 9/1926 | Nauth | 128/346 |
| 1,920,821 | 8/1933 | Wassengar | 128/92 VZ |
| 1,985,108 | 12/1934 | Rush | 128/346 |
| 2,238,660 | 4/1941 | Santora | 128/346 |
| 2,362,957 | 11/1944 | Hackett | 128/346 |
| 2,427,128 | 9/1947 | Ettinger | 128/92 VZ |
| 2,583,896 | 1/1952 | Siebrandt | 128/346 |
| 3,006,344 | 10/1961 | Vogelfanger | 128/318 |
| 3,835,861 | 9/1974 | Kees, Jr. et al. | 128/346 |
| 3,856,016 | 12/1974 | Davis | 128/325 |
| 3,868,957 | 3/1975 | Doddington | 128/346 |
| 4,064,881 | 12/1977 | Meredith | 128/325 |
| 4,106,508 | 8/1978 | Berlin | 128/346 |
| 4,146,022 | 3/1979 | Johnson et al. | 128/92 VK |
| 4,169,476 | 10/1979 | Hiltebrandt | 128/325 |
| 4,187,840 | 2/1980 | Watanabe | 128/92 |
| 4,457,306 | 7/1984 | Borzone | 128/303 R |
| 4,569,131 | 2/1986 | Falk et al. | 30/251 |
| 4,574,803 | 3/1986 | Storz | 128/305 |
| 4,574,804 | 3/1986 | Kurwa | 128/322 |
| 4,633,862 | 1/1987 | Petersen | 128/92 VZ |

FOREIGN PATENT DOCUMENTS 2140735 12/1984 United Kingdom .

Primary Examiner—John D. Yasko

[57] ABSTRACT

Disclosed is a clamp which comprises a pair of hook-shaped fixed prongs formed at the distal end of an elongated clamp body. Mounted longitudinally in the clamp body is a moveable prong which reciprocates in relation to the distal end of the clamp body and the fixed prongs. The inside surfaces of the hook-shaped fixed prongs face the moveable prong and are also disposed so that the moveable prong moves in a direction lying between the pair of fixed prongs. A pair of arms is used to control the clamp, with one arm connected to the moveable prong while the other is fixedly connected with the clamp body. To engage a sesamoid bone, the moveable prong is moved toward the two fixed prongs thereby clamping the bone between the three prongs. The arrangement of the prongs results in the bone being hooked and cradled.

19 Claims, 2 Drawing Sheets

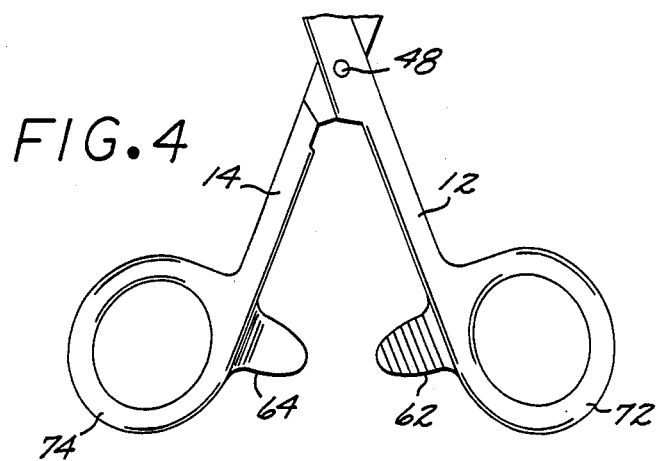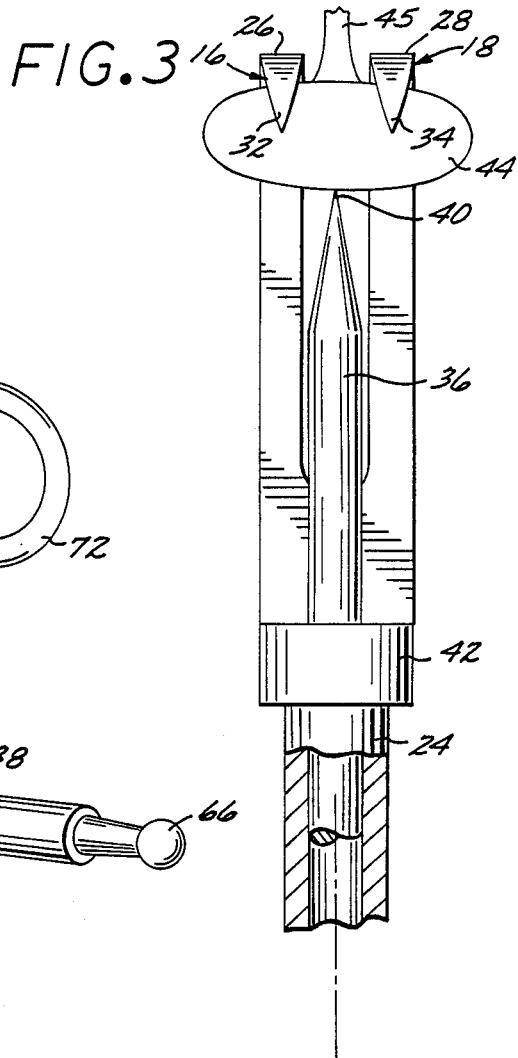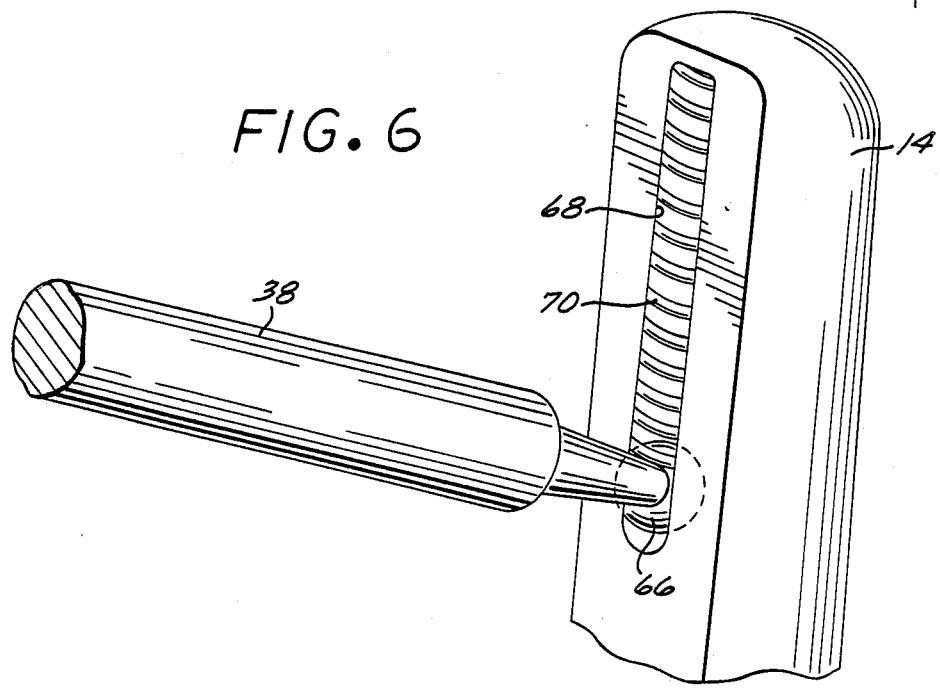

SESAMOID BONE CLAMP

BACKGROUND OF THE INVENTION

The invention relates to surgical instruments, and more particularly, to instruments used for clamping bones.

The sesamoid bones are a pair of accessory bones located under the first metatarsal head of each foot. They are typically oval in shape and are invested in the tendons of the flexor hallucis brevis muscle. In certain cases, the resection of a sesamoid bone or sesamoidectomy may be undertaken. Access to the lateral sesamoid bone is typically from the dorsal side of the foot and through the first interspace between the first and second metatarsals. The approach is a vertical, top to bottom approach in the sagittal plane and difficulty many times occurs in manipulating instruments for resection due to the limited space available between the first and second metatarsals.

In a prior technique, a stab incision is made between the sesamoid bone and the metatarsal head. At this time, the sesamoid bone is not clamped. The incision is then extended proximally and distally. A thumb and forefinger forceps is then used to grasp the conjoined tendon of Adductor Hallucis and the sesamoid bone is peeled from it by use of a scalpel. The sesamoid bone is then removed with the forceps. Problems have arisen with this method in that the sesamoid bone tends to rotate away from the scalpel and consequently, the chances of inadvertent cutting of the Flexor Hallucis Longus tendon and other surrounding tissues are increased.

In another prior technique, a clamp is used to engage the distal and proximal ends of the sesamoid bone. The engaged clamp is used to position the sesamoid bone during use of the scalpel and is used to remove the resected sesamoid bone. The clamp has two arms which pivot in relation to each other and has hooks formed at the ends of the arms which are used to engage the ends of the sesamoid bone. Because of its configuration and the angle at which it is applied, this clamp has been found to interfere with certain surgical operations involved in the sesamoidectomy. Performance of some surgical operations at an awkward angle results. Additionally, since the clamp must be large enough to reach the ends of the sesamoid bone and since it remains engaged with the bone during its removal, the size of the incision may be increased to accommodate the clamp. This increased incision size has been found to be undesirable. Another disadvantage of this type of clamp is the tenuous grip it provides on the sesamoid bone which is generally oval shaped and is slippery during surgery. In using this prior technique clamp which grips the ends of the sesamoid bone, slippage of the bone out of the clamp has been experienced during removal of the resected bone.

It would be useful to be able to clamp the sesamoid bone during certain uses of the scalpel in a sesamoidectomy so that it does not rotate away or otherwise move except as desired. This would provide greater control and decrease the chances of inadvertent cutting of surrounding tissues. Various surgical clamps, such as those described above, have been used for sesamoidectomies, however, such clamps have had disadvantages. It would be a valuable contribution to the art to provide a clamp which, when used in a sesamoidectomy or similar type of operation, would be applied through a plane perpendicular to the incision plane so that interference with surgical operations is lessened. It would also be valuable to provide a clamp which does not require a larger incision to be made and which provides a more positive grip on the clamped object.

SUMMARY OF THE INVENTION

In accordance with the invention, there is provided a clamp which may be used to clamp a bone and which is particularly useful for clamping a sesamoid bone. Disposed at the distal end of the clamp are multiple prongs which are fixedly attached to the clamp body and are hook-shaped such that they extend in a direction away from the clamp body and then curve back towards it. In relation to each other, the fixed prongs face in the same general direction. Opposing them is a moveable prong. In the embodiment disclosed, this moveable prong is slidably mounted in the clamp body so that it reciprocates towards and away from the fixed prongs. When slid towards the fixed prongs, this moveable prong functions to secure the clamped object between itself and the fixed prongs. The operation of the fixed prongs is such that they hook and cradle the clamped object. An appropriate amount of pressure is applied against the object by the moveable prong to keep the object in contact with all of the prongs thereby securing the object in a desired position. In the preferred embodiment, the prongs are sharpened so that a more positive grip on the clamped object is provided.

The disclosed embodiment of the clamp also includes two arms which are pivotally interconnected to form a scissors-like grip for users of the clamp. The relative movement of the arms controls the relative movement of the fixed and moveable prongs. One arm is immoveably coupled to the clamp body while the other arm is coupled to the moveable prong so that the scissors-like motion of the arms is translated into the reciprocating motion of the moveable prong. Each arm has a handle at its distal end. A latching mechanism may be included for locking the arms in a particular position in relation to each other thereby fixing the position of the moveable prong in relation to the fixed prongs. The locked position is selected based upon the size of the particular object to be clamped between the prongs as well as the amount of pressure to be exerted against that object by those prongs.

In the disclosed embodiment, the moveable prong is formed on one end of a rod which is disposed within the clamp body for sliding therethrough such that reciprocation of the prong may be effected. At the opposite end, the rod is coupled to one of the arms. When the handles of the arms are moved together towards the closed position, the moveable prong is caused to extend further from the clamp body and move towards the fixed prongs. When the handles are moved apart towards the open position, the moveable prong is caused to move away from the fixed prongs and recede into the clamp body. The pivot point of the arms is selected such that the desired range of movement of the moveable prong is achieved with the available amount of movement of the arms.

In the preferred embodiment, the moveable prong is located longitudinally through the clamp body in approximately its center. There are two hook-shaped, fixed prongs which are attached at their shanks towards the bottom of the clamp body below the moveable prong. The fixed prongs extend outwardly in relation to the clamp body from their point of attachment and then curve back towards the top of the clamp body such that the tips of the fixed prongs are above the moveable prong. The moveable prong is thus disposed at a position between the tips of the fixed prongs and their points of attachment in relation to the clamp body. By this arrangement, the object being clamped is urged in the direction of the two fixed prongs by the moveable prong at a point approximately centered between the two extremes of each fixed prong. The tips of the fixed prongs will restrict movement of the object at points above the moveable prong and the shanks of the fixed prongs will restrict movement at points below the moveable prong. Also, since the fixed prongs are hook-shaped, they will provide pressure against the side of the object opposite the moveable prong. The arrangement of the invention thus secures the clamped object from movement in the directions discussed.

In the disclosed embodiment, the two fixed prongs are separated from each other over a portion of their lengths and are located at positions on either side of and equidistant from the longitudinal centerline of the clamp body. Since the moveable prong is located along the longitudinal centerline of the clamp body, it will move in a plane lying approximately midway between the fixed prongs. In the case of a clamped object which is oval in shape, such as the typical sesamoid bone, the curved shanks of the two fixed prongs will cradle the bone which is urged towards them by the moveable prong, and since the moveable prong is approximately centered between the fixed prongs, they will resist twisting motion of the bone.

The clamp body is formed to be long enough to extend past the width of the typical foot. The arms are disposed on the side of the longitudinal centerline of the clamp body opposite the side on which the tips of the fixed prongs are disposed. In use, the clamp is applied to the sesamoid bone from underneath it and when engaged, the arms will be pointing towards the bottom of the foot. The clamp will therefore be approximately perpendicular to the surgical plane and the clamp will only slightly, if at all, be located in the incision area.

The disclosed clamp has a further feature relating to the separation between the fixed prongs along a portion of their length. Because of this separation, there is space between the fixed prongs in which a scalpel may be used for cutting the ligament on the medial aspect of the sesamoid bone. Thus, the clamp may remain attached and resection is facilitated.

BRIEF DESCRIPTION OF THE DRAWINGS

For a more detailed description, reference is now made to the following description of the preferred embodiment and the accompanying drawings wherein:

FIG. 3 is a top view of the distal end of the clamp shown in FIGS. 1 and 2, and also shows an object being clamped;

FIG. 4 is a view of a latching mechanism usable on the arms shown in FIGS. 1 and 2;

FIG. 5 is a view of the proximal portion of the reciprocating rod showing a structure for use in coupling the rod to an arm; and FIG. 6 is a view of the coupling mechanism shown in side view in FIG. 1 which is usable in the invention to transmit the pivotal motion of the arms to the reciprocating motion of the moveable prong.

DETAILED DESCRIPTION OF THE PREFERRED EMBODIMENT

Figure 1:
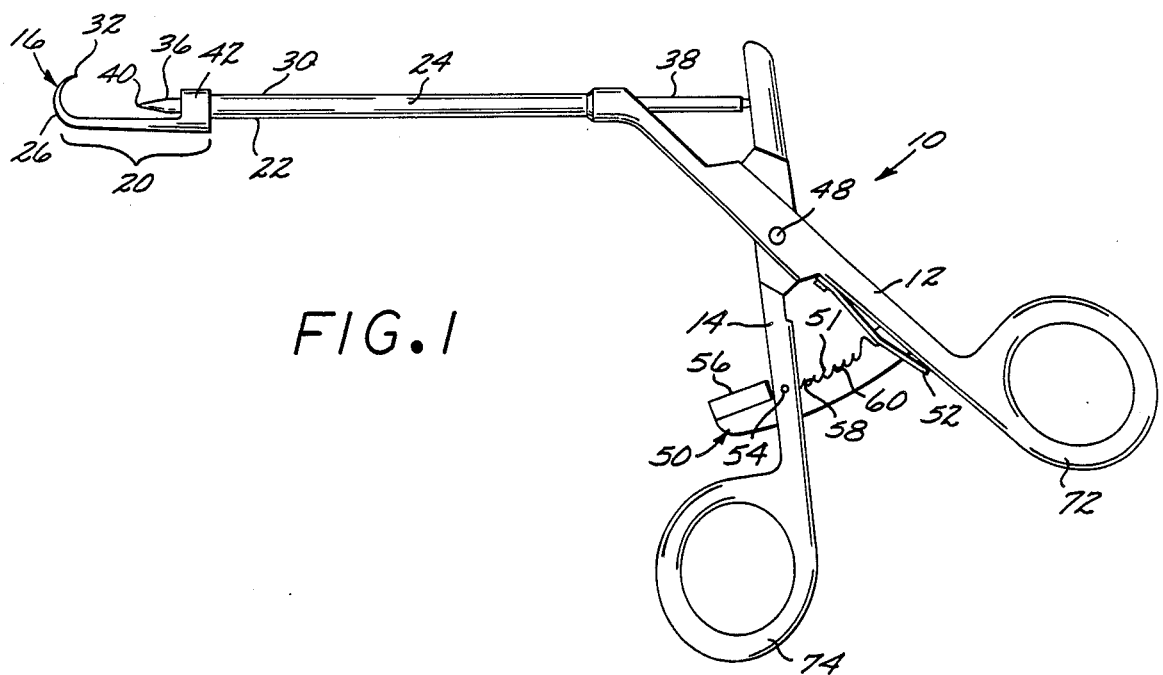
FIG. 1 is a side view of a clamp in accordance with the invention. The handles of the clamp are shown in an open position.
Figure 2:
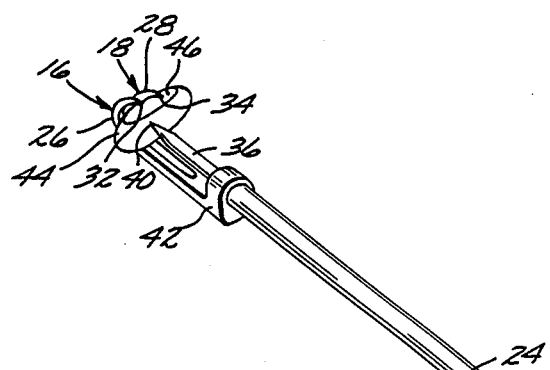
FIG. 2 is a perspective view of the clamp of FIG. 1 showing the handles in a closed position and the prongs clamping an object resembling a sesamoid bone.
Figure 2:
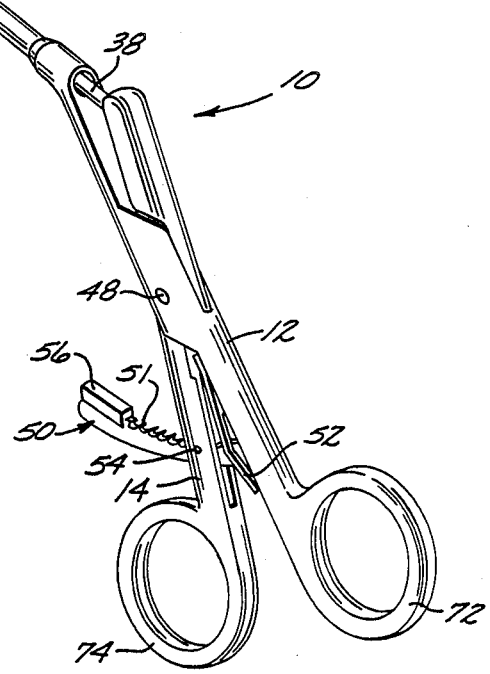

Referring now to the drawings with more particularity, FIGS. 1 and 2 present views of a clamp 10 in accordance with the invention. FIG. 1 shows the arms 12,14 in an open position while FIG. 2 presents a perspective view of FIG. 1 with the arms 12,14 in a closed position. In this embodiment, a pair of fixed prongs 16,18 are disposed at the distal end 20 of the clamp 10. These prongs 16,18 are attached towards the bottom 22 of the clamp body 24 and have shanks 26,28 which extend outwardly in relation to the clamp body 24 and then curve back towards the top 30 of the clamp body 24. By this configuration, they resemble open hooks. The term "shank" is used in a broad sense herein and includes the elongated shaft of the prong from its tip to its point of coupling with another member. In this embodiment, the fixed prongs 16,18 each include a pointed tip 32,34 which face in the same general direction and both prongs 16,18 are substantially parallel to one another. AAs shown in FIG. 1, the tips 32,34 of the fixed prongs 16,18 are disposed above a third prong 36 which is moveable and which extends from the clamp body 24 at its distal end 20.

The moveable prong 36 is mounted in the clamp body 24 along its longitudinal centerline so that it opposes the fixed prongs 16,18 and is capable of reciprocation towards and away from the fixed prongs 16,18. In the preferred embodiment, the moveable prong 36 is formed at one end of a rod 38 and as with the fixed prongs 16,18, has a pointed tip 40. As shown in FIGS. 1, 2, and 3, the moveable prong 36 is mounted inside the clamp body 24 and is slidable through it thus enabling a reciprocating motion in relation to the fixed prongs 16,18. The amount of extension of the moveable prong 36 from the distal end of the clamp body 24 is selected to be sufficient to engage the clamped object and apply enough pressure against the object to secure it between the prongs.

In the embodiments shown in FIGS. 1, 2, and 3, the clamp body 24 is cylindrically shaped. The fixed prongs 16,18 are shown attached to the clamp body 24 at its distal end 20 by means of a collar type of structure 42. As shown, the collar 42 is arranged such that the fixed prongs 16,18 attach to it at positions towards the bottom 22 of the clamp body 24. The collar 42 may be a separate member which is attached to the clamp body 24, or may be a part of the clamp body 24. When it is a member which is attached to the clamp body, it may be so attached by means known in the art such as silver soldering. Although a collar type of structure is shown, this is not meant to be restrictive of the invention. The fixed prongs may be attached to the clamp body by other means such as by direct attachment or may be formed as part of the clamp body.

The shanks 26,28 of the fixed prongs 16,18 extend outwardly from the collar 42, then curve upwards, and then curve inwards towards the clamp body 24 and terminate at their respective prong tips 32,34 which are disposed above the longitudinal centerline of the clamp body and therefore, the moveable prong 36. Thus, as shown in FIG. 1, the moveable prong 36 is disposed in a plane lying between the tips 32,34 of the fixed prongs 16,18 and the points of coupling of the fixed prongs 16,18 in relation to the clamp body 24. In the preferred embodiment, the moveable prong lies midway between the tips and point of coupling of the fixed prongs. By this arrangement, an object to be clamped, such as the object 44 shown in FIGS. 2 and 3, will be urged towards the fixed prongs 16,18 by the moveable prong 36 and will be hooked and cradled by the fixed prongs 16,18. As shown, the tips 32,34 of the fixed prongs 16,18 will resist upward motion of the object 44 while the shanks 26,28 of the fixed prongs 16,18 will resist downward and longitudinal motions of the object 44. As used herein, longitudinal motion refers to that motion in the direction of movement of the moveable prong.

It has been found to be of value to have the shanks 26,28 of the fixed prongs 16,18 separate from each other from their points of attachment with the collar 42 to their tips. Not only does this feature facilitate insertion and engagement of the clamp during a sesamoidectomy, it permits cutting at the bottom and sides of the sesamoid bone. However, other configurations are possible. In one variation, the fixed prongs may be part of a fixed prong member which may take other forms. For example, the fixed prong member may comprise a solid piece extending from the collar 42 or from the clamp body 24 until encountering the curved portion of the shank, and then separate into two prongs.

As shown in FIG. 3, the moveable prong 36 is disposed in a plane lying approximately midway between the fixed prongs 16,18 and when reciprocating, does so in this plane. The opposing shanks of the fixed prongs 16,18 will function to contain the clamped object 44 from motion in the longitudinal direction. Since there are two fixed prongs 16,18 in this embodiment, and the moveable prong 36 is centrally disposed between them, twisting motion of the clamped object 44 will be resisted by the curved shanks 26,28 of these fixed prongs 16,18. If the object is large enough and if enough pressure is applied by the moveable prong 36, its sharpened tip 40 and the sharpened tips of the tips 32,34 of the fixed prongs 16,18 may pierce the object 44 thus providing a more positive grip. In FIGS. 2 and 3, an application of the clamp 10 in accordance with the invention is shown. The object 44 is in the shape of a sesamoid bone. As is shown, the moveable prong 36 is in contact with the medial aspect of that object 44 and is urging it into contact with the fixed prongs 16,18 which hook and cradle it.

In viewing the object 44 shown in FIG. 2 as representative of a sesamoid bone, the top 46 of the object 44 would be adjacent or attached to a metatarsal head. The clamp 10 therefore is applied to the sesamoid bone from underneath it, i.e., to the side opposite the metatarsal head. The tips 32,34 of the fixed prongs 16,18 grasp the sesamoid bone near its point of attachment in relation to the metatarsal head while the curved portion of the shanks 26,28 are disposed across the bone's medial aspect and the straight portions of the shanks 26,28 extend under the bone. The clamp 10 is out of the way of cutting to be performed at the top 46 of the bone 44, but still provides a firm grasp of the bone 44. As previously mentioned, a further feature of the invention is the separation between the shanks 26,28 of the fixed prongs 16,18 at the medial aspect of the object 44. This separation facilitates the cutting of the intersesamoidal ligament 45 shown in FIG. 3 when the clamp 10 is engaged with a sesamoid bone. Thus, in the case of the typical sesamoidectomy, the clamp 10 in accordance with the invention need not be removed to cut this ligament.

The clamp body 24 in the preferred embodiment is formed to be long enough to extend past the width of the typical foot. The arms 12,14 shown in FIGS. 1 and 2 extend from the clamp body 24 in a direction from the longitudinal centerline of the clamp body opposite the direction from the longitudinal centerline in which the curved portions of the fixed prongs 16,18 extend. Arm 12 and arm 14 are shown as each having a handle 72,74 respectively, at their ends. As shown in FIGS. 1, 2, and 4, these handles 72,74 comprise looped ends of the arms 12,14. In use, when the prongs have engaged the sesamoid bone as described above, the arms 12,14 will be pointing towards the bottom of the foot. Since the clamp 10 in accordance with the invention is applied to the sesamoid bone from the underneath direction as discussed, and the arms 12,14 are attached to the clamp 10 such that they will point towards the bottom of the foot, the clamp 10 will only slightly, if at all, be located in the incision area. The clamp's position will therefore be approximately perpendicular to the surgical plane. Since the arms are disposed at the bottom of the clamp and the clamp body extends past the width of the patient's foot, the arms of the clamp and the hand of the user controlling the arms will not interfere with the surgical operations. One of the surgeon's hands may be applied to the clamp handles to control the position of the engaged clamp and thereby the position of the sesamoid bone while the other is free for resection. In certain situations, the clamp may be left to rest on the patient's foot with the bone being held in position by means of the weight of the clamp.

In the preferred embodiment, two arms in a scissors-like relationship are used to control the position of the clamp body and the movement of the moveable prong. As shown in FIGS. 1 and 2, the inner arm 14 is coupled to the rod 38 and the outer arm 12 is immoveably coupled to the clamp body 24. In the embodiment shown in these two figures, the inner arm 14 extends past the pivot point 48 and couples to the rod 38. The outer arm 12 extends past the pivot point 48 and is immoveably attached near the proximal end of the clamp body 24. The outer arm 12 may be coupled to the clamp body 24 by techniques known to those skilled in the art such as by silver soldering. By the arrangement of the invention, pivoting the arms 12,14 in relation to each other, will cause the rod 38 to slide in the clamp body 24 and therefore, will cause the moveable prong 36 formed thereon to move in relation to the fixed prongs 16,18.

Two latching means are shown in FIGS. 1, 2, and 4 for use in positioning the arms 12,14. In the latching mechanism shown in FIGS. 1 and 2, a member 50 having sawtooth type serrations 51 on its upper edge is attached to the outer arm 12 and is disposed through the inner arm 14. Also attached to the outer arm 12 is a spring 52 for urging the latching member 50 in the direction of the pivot point 48. The inner arm 14 includes a transverse pin 54 which is engaged by the serrations 51 of the latching member 50. Formed on the end of the latching member 50 is a release handle 56 for urging the latching mechanism downwards and against the spring 52 thereby disengaging the latching member 50 from the transverse pin 54. The spring 52 of the latching mechanism urges the latching member 50 upwards to engage the transverse pin 54 with one of its serrations.

The sawtooth serrations are oriented such that the relatively gentle rising edges 58 of the sawteeth are disposed towards the distal end of the clamp body 24. Thus, the arms may be closed relatively freely since these edges 58 are encountered by the transverse pin 54. However, when being opened, the concavely shaped edges 60 of the sawteeth are encountered by the transverse pin 54 and cause the latching effect. In order to open the arms 12,14, the release handle 56 must be depressed. In accordance with this latching mechanism, the arms 12,14 may not be opened until the release handle 56 is depressed appropriately.

A second latching mechanism useable in the invention is shown in FIG. 4. In this mechanism, each arm 12,14 has a latching extension 62,64 respectively which extends towards the other arm. On opposing faces of the latching extensions 62,64 are formed serrations. These serrations are also of a sawtooth type shape and are oriented on the latching extensions such that the edges which form an obtuse angle will engage each other when the arms are being opened. In order to disengage this latching mechanism, the arms must be moved laterally until the serrations actually disengage from one another and then the arms may be opened.

A mechanism for coupling the inner arm 14 to the rod 38 and so to the moveable prong 36 is shown in more detail in FIGS. 5 and 6. In FIG. 5, the proximal end of the rod 38 is shown as having a ball 66 formed on it. This ball may be formed from the rod or may be attached to it by means known to those skilled in the art such as silver soldering. As shown in FIG. 6, a channel 68 is formed in the upper part of the inside arm 14. By inserting the ball 66 into the channel 68, a type of sliding ball joint is formed. The channel 68 is formed to be long enough to allow for the necessary amount of movement of the ball 66 to translate the pivotal motion of the arms 12,14 into the sliding motion of the rod 38 and therefore the moveable prong 36. By this ball joint means, the moveable prong 36 is pushed towards the fixed prongs 16,18 when the arms 12,14 are closed, and is pulled away from the fixed prongs 16,18 when the arms 12,14 are opened thus resulting in reciprocation of the moveable prong 36. In FIG. 6, a spring 70 is shown installed in the channel 68 above the ball 66 for urging the ball 66 towards the pivot point 48 of the arms 12,14. This spring 70 will have the effect of urging the arms 12,14 into the open position.

A working embodiment was made and had the following dimensions. Two fixed prongs 16,18 were used and were approximately 1.5 mm (0.06 inches) in diameter and the spacing between them at the collar 42 was approximately 4.0 mm (0.16 inches). The moveable prong 36 was approximately 3.0 mm (0.12 inches) in diameter. The moveable prong 36 reciprocation stroke was approximately 3.0 mm (0.51 inches). When in the fully retracted position, the moveable prong 36 was located approximately 14.0 mm (0.55 inches) from the furthest point of the inner portion of the shanks 26,28. The distance from the clamp body 24 to the furthest point of the inner portion of the shanks 26,28 was approximately 22.9 mm (0.90 inches). The angle of the tips 32,38 of the fixed prongs 16,18 from the tip 40 of the moveable prong 36 was approximately 60 degrees when the moveable prong was in its fully extended position. The diameter of the clamp body was 7.0 mm (0.28 inches). The length of the clamp body was 94.0 mm (03.7 inches). The clamp body, prongs, and arms were formed of surgical stainless steel for sterilization purposes.

Although a preferred embodiment of the invention has been described and shown in detail, it is anticipated that modifications and variations may occur to those skilled in the art which do not depart from the inventive concepts. Accordingly, it is intended within the appended claims to cover all such modifications and variations which come within the scope of the invention.

What is claimed is:

1. A clamp comprising:
   an elongated body member having a distal end and having a proximal end opposite the distal end;
   a plurality of fixed prong members rigidly coupled to the distal end of the body member and each fixed prong member having a tip;
   an elongated moveable prong member having an end on which is formed a tip, the moveable prong member being mounted in the body member such that it is longitudinally slidable therein said such that the moveable prong tip extends from the distal end of the body member for reciprocating in relation to the distal end;
   the fixed prong members being hook-shaped with the inside surfaces of the hook-shape facing towards the tip of the moveable prong member, and being disposed so that the moveable prong moves in a direction lying between the fixed prong members;
   arm means for controlling the body member and for controlling the movement of the moveable prong member in relation thereto so that the moveable prong member may be reciprocated, said arm means comprising a first arm rigidly coupled to the body member at the proximal end thereof and a second arm coupled to the moveable prong member; and
   pivoting means for pivotally coupling said arms to each other.

2. The clamp of claim 1 wherein each of the fixed prong members is shaped so that the plane in which the moveable prong moves intersects the hook shape at approximately its center.

3. The clamp of claim 1 wherein:
   each of said arms has a handle; and
   said pivoting means couples the arms to each other so that bringing together the handles results in moving the moveable prong member towards the fixed prong members.

4. The clamp of claim 2 wherein the arm means extend from a side of the body member which is opposite to the side on which the tips of the fixed prong members are located.

5. The clamp of claim 1 wherein the fixed prong members comprise two prongs which have a preselected amount of separation between them at the locations of their hook-shapes intersected by the plane in which the moveable prong member moves.

6. The clamp of claim 1 wherein:
   the elongated body member comprises a passage formed longitudinally therein; and
   the moveable prong members being formed on an end of a rod, the rod being slidably disposed in the passage for movement therein.

7. The clamp of claim 6 wherein the passage is located approximately along the centerline of the body member.

8. The clamp of claim 7 wherein:

the rod comprises a distal end at which the moveable prong member is formed and a proximal end; and coupling means for coupling the second arm to the proximal end of the rod.

9. The clamp of claim 8 wherein the coupling means comprises a spring means for urging the moveable prong member towards a retracted position in relation to the body member.

10. The clamp of claim 1 further comprising latching means for securing the arms in a selected fixed position in relation to each other.

11. A clamp comprising:

an elongated body member having a passage formed longitudinally therethrough and having a distal end and having a proximal end opposite the distal end;

a pair of fixed prong members rigidly coupled to the distal end of the body member and each fixed prong member having a tip;

a substantially straight rod having a moveable prong formed at a first end and disposed coaxially therewith, said rod being slidably mounted in the longitudinal passage through the body member, the rod being disposed so that the moveable prong extends from the distal end of the body member for reciprocating in relation to the distal end;

the fixed prong members being hook-shaped with the inside surfaces of the hook-shape facing towards the moveable prong, and having a preselected amount of separation between them at the locations of their hook shapes which are intersected by the plane in which the moveable prong moves, and further, being disposed so that the moveable prong moves in a direction lying between the fixed prong members;

a pair of arms, one of which is fixedly coupled to the body member, the other of which is coupled to the moveable prong for controlling the movement of the moveable prong, the arms extending from a side of the body member which is opposite to that side on which the tips of the fixed prong members are located;

means for pivotally connecting the arms together so that bringing together the handles results in moving the moveable prong toward the fixed prong members; and latching means for securing the arms in a selected fixed position in relation to each other.

12. The clamp of claim 11 wherein each of the fixed prong members is shaped so that the plane in which the moveable prong moves intersects the hook shape at approximately its center.

13. The clamp of claim 1 wherein the tip of each fixed prong member and the tip of the moveable prong member are pointed.

14. The clamp of claim 4 wherein the first arm forms an obtuse angle with the body member.

15. The clamp of claim 11 wherein the tip of each fixed prong member and the tip of the moveable prong member are pointed.

16. The clamp of claim 12 wherein the first arm forms an obtuse angle with the body member.

17. A clamp for gripping an object comprising:

an elongated body member having a distal end and having a proximal end opposite the distal end;

a plurality of fixed prong members being rigidly coupled to the distal end of the body member;

a substantially straight rod being mounted in the body member such that it is longitudinally slidable therein and having a first end which extends from the distal end of the body member;

the fixed prong members being hook-shaped with the inside surfaces of the hook-shaped facing toward the first end of the rod, and being disposed so that the rod moves in a direction lying between the fixed prong members such that the object may be gripped between said fixed prong members and said rod;

arm means for controlling the movement of the rod in relation to the body member, said arm means comprising a first arm rigidly coupled to the body member and a second arm coupled to the moveable prong member; and pivoting means for pivotally coupling said arms to each other.

18. The clamp of claim 17 wherein the first end of the rod is pointed.

19. The clamp of claim 17 wherein the rod is substantially circular in cross section and the first end of the rod is pointed.

* * * * *